United States Patent
Gergeley (12)

(10) Patent No.: US 7,322,931 B2
(45) Date of Patent: Jan. 29, 2008

(54) SONOGRAPHY GUIDED EMBYRO TRANSFER FOR IN VITRO FERTILIZATION

(76) Inventor: Robert Z. Gergeley, 450 N. Roxbury Dr., Beverly Hills, CA (US) 90210

( * ) Notice: Subject to any disclaimer, the term of this patent is extended or adjusted under 35 U.S.C. 154(b) by 0 days.

(21) Appl. No.: 11/131,903

(22) Filed: May 17, 2005

(65) Prior Publication Data

US 2005/0261546 A1    Nov. 24, 2005

Related U.S. Application Data

(60) Provisional application No. 60/572,267, filed on May 17, 2004.

(51) Int. Cl.
*A61B 17/435* (2006.01)

(52) U.S. Cl. .......................................... 600/33; 600/34

(58) Field of Classification Search ................. 600/33, 600/34, 551; 128/916, 922; 604/264
See application file for complete search history.

(56) References Cited

U.S. PATENT DOCUMENTS 6,375,616 B1 * 4/2002 Soferman et al. ........... 600/443
2004/0106869 A1 * 6/2004 Tepper ....................... 600/443

OTHER PUBLICATIONS

Yamashita, Y. et al., The Outcome of Repeated In Vitro Fertilization-Embryo Transfer Based on the Endometrial Thickness, 2003. Bulletin of the Osaka Medical College, 49 (1,2): 5-9.*
Mansour, R.T. et al, Optimizing the embryo transfer technique, 2002. Human Reproduction, vol. 17, No. 5, pp. 1149-1153.*

* cited by examiner

*Primary Examiner*—Charles A. Marmor, II
*Assistant Examiner*—Christine D. Hopkins
(74) *Attorney, Agent, or Firm*—Jones Day (57) ABSTRACT

The present provides novel systems and methods to facilitate embryo transfer, to maximize implantation rates and to improve pregnancy rates resulting from In Vitro fertilization.

2 Claims, 6 Drawing Sheets

SONOGRAPHY GUIDED EMBYRO TRANSFER FOR IN VITRO FERTILIZATION

This application claims the benefit of U.S. Provisional Application No. 60/572,267, filed May 17, 2004.

FIELD OF THE INVENTION

The current invention generally relates to systems and methods for in vitro fertilization, and more specifically, to the use of ultrasound to implant an embryo at an optimal location in the uterine cavity.

BACKGROUND OF THE INVENTION

The success rates in patients undergoing In Vitro Fertilization (IVF) has improved tremendously over the past few years. Better ovulation induction protocols as well as great improvements in the IVF laboratory have greatly contributed to the increased pregnancy rate. One area that has received more attention than usual is the embryo transfer technique. While many variations exist in the preparation of the cervix, the type of transfer catheter used, the duration of the transfer and the use of trial transfers, most physicians in the United States as well as other countries are now performing embryo transfers under ultrasound guidance. Since the introduction of the ultrasound as an aid to embryo transfer, physicians have reported a greater ease of transfer, and more accurate placement of the embryos within the uterine cavity. The patients also enjoy watching their embryos, distracting them from the actual transfer procedure.

Ultrasound guided embryo transfer has been around since 1985, however it has become almost universal in the past three years. Since then, multiple studies have shown higher pregnancy rates when performing embryo transfers in conjunction with ultrasonography (1-4). The advantages of ultrasound guided embryo transfers include the facilitation of embryo transfer as well as physician's ability to visualize catheter and embryo placement.

Although 2D ultrasound guidance has been increasingly utilized, controversy exists regarding the ideal placement of the embryos within the uterine cavity. Various studies have been published in regards to the ideal area of embryo transfer. However these studies only represent generalized locations, not taking into consideration that uterine anatomy varies among women.

Integral to a successful in vitro fertilization (IVF) is the placement of the embryo in the uterine cavity. The transfer of an embryo from the laboratory to the uterus is generally referred to as embryo transfer. Embryo transfer is generally the final step in an IVF cycle, and a successful embryo transfer is a prerequisite for achieving pregnancy. While the IVF technology and success rates have come a long way, there still remains room for improvement. The pregnancy rate is highly influenced by the quality of the embryos, the receptivity of the endometrium and by the transfer technique (5).

Because of the importance of the embryo transfer phase, efforts have been made since the introduction of IVF approximately twenty years ago to determine the "best spot" within the uterine cavity to implant the embryo. Two dimensional (2D) sonography has been used for some time to aid in embryo transfer. While this represented an advance over implanting embryos without any guidance whatsoever, two dimensional sonography has still only provided guidance as to the general area at which the embryo should be released for implantation. There is still no consensus of what the ideal choice for implantation is for embryos. In a study by Baba et al, embryos were transferred to the midfundal area in 60 patients. Among the 22 pregnancies, 80% of the embryos implanted in the areas to which they were transferred, while 20% implanted in other areas (6).

Other studies have been published suggesting various locations within the uterine cavity where embryos should be released. These studies have suggested implantation in locations ranging from the lower uterine segment, to various distances (0.5 cm-2.0 cm) from the uterine fundus. However, these distances still only represent generalized locations. Furthermore, the value to place on these distances as guidelines decreases when considering that the configuration and dimensions of the uterine cavity vary between women. The location of embryo transfer in respect to the uterine anatomy also varies among physicians. Some studies have shown that the optimal location for embryo transfer is 0.5-1 cm away from the uterine fundus (3), while some believe that the tip of the catheter should be 1.5 cm from the uterine fundus (2). However, others have shown that transfer should be in the lower to middle uterine segment (7). In a different study by Pope et al, it was demonstrated that for every additional millimeter the embryos are placed away from the uterine fundus, the clinical pregnancy rate increases by 11% (8). In a recent randomized study by Franco et al, embryos were deposited in the lower or upper half of the endometrial cavity and there was no difference in pregnancy or implantation rates (9).

In sum, two dimensional sonography does not provide the clinician with an optimal view of where the embryo should be released. Accordingly, there exists a need for a more accurate system with which to determine the optimal location at which to implant an embryo. There also exists a need for embryo transfer to be carried out with less trauma to the woman undergoing IVF.

SUMMARY OF THE INVENTION

An aspect of the invention is determining the optimal location at which to implant an embryo. In the discussion below, this is referred to as the Maximum Implant Potential point, or MIP point.

Another aspect of the invention is the use of three and four dimensional ultrasound to view the uterine cavity to determine the MIP point, and to help guide the clinician's catheter to the MIP point when implanting embryo(s).

Another aspect of the invention is the overall procedure involving the use of an ultrasound machine to implant embryo(s) in an IVF cycle.

A further aspect of the invention is an integrated system for the determination of the most suitable implantation point so as to maximize fertilization rates in individual women.

DESCRIPTION OF THE PREFERRED EMBODIMENTS

Figure 1:
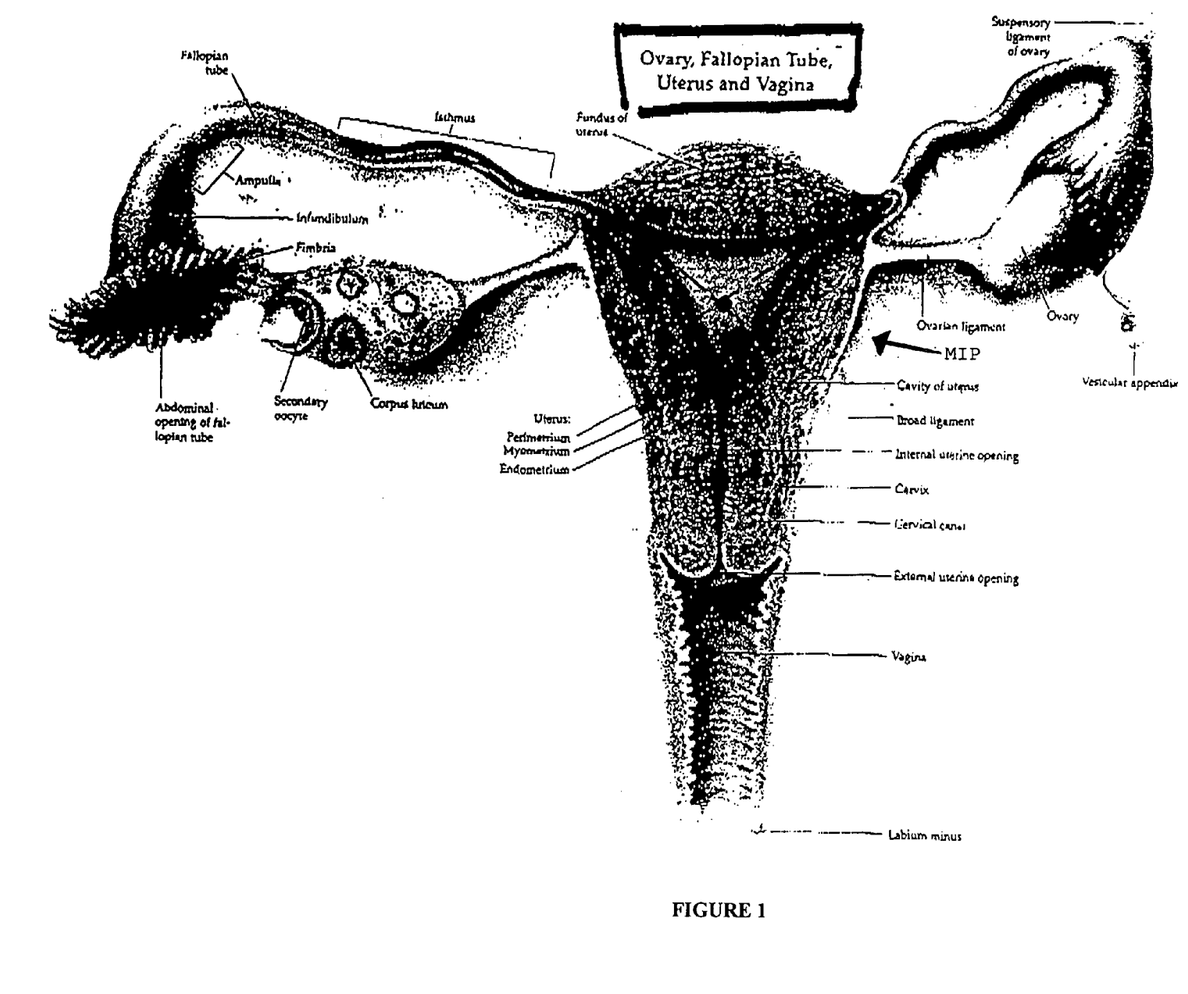
FIG. 1 is a cross-section of the female reproductive system. The location of the MIP is as indicated.
Figure 4:
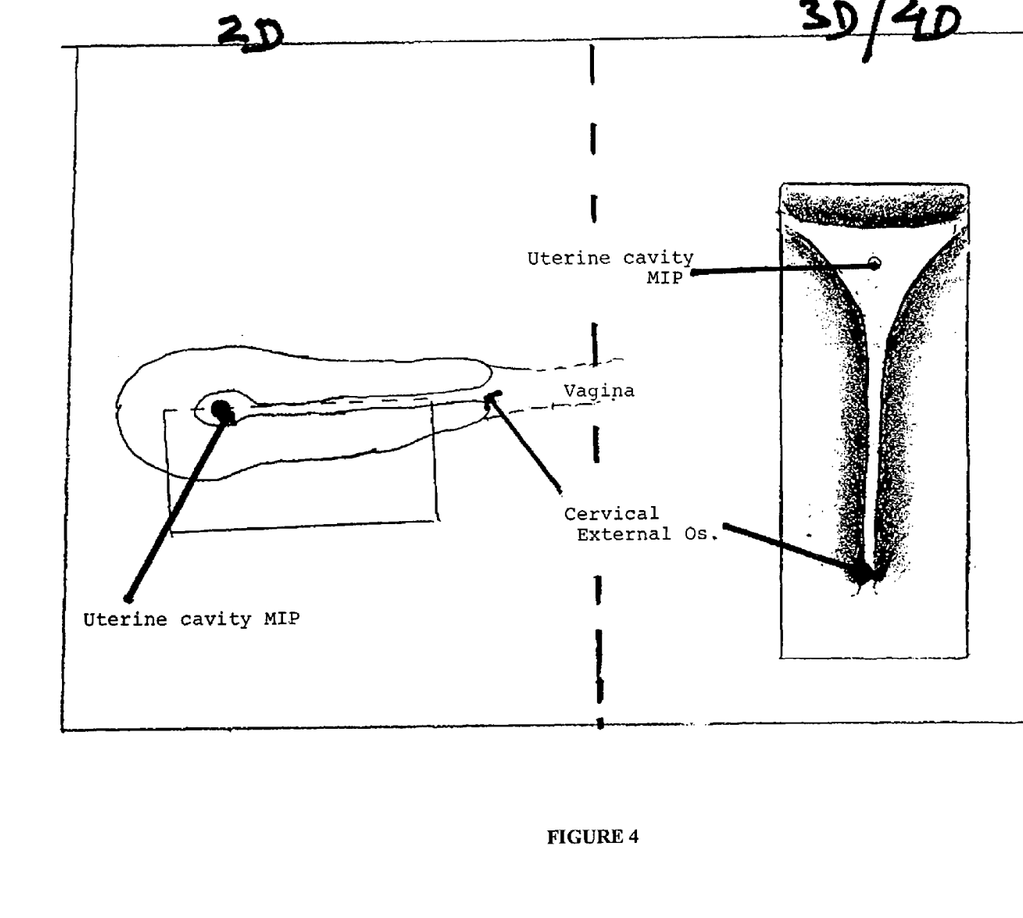
FIG. 4 represents a split screen of an ultrasound machine showing two dimensional and three/four dimensional views of the uterine cavity.
Figure 5:
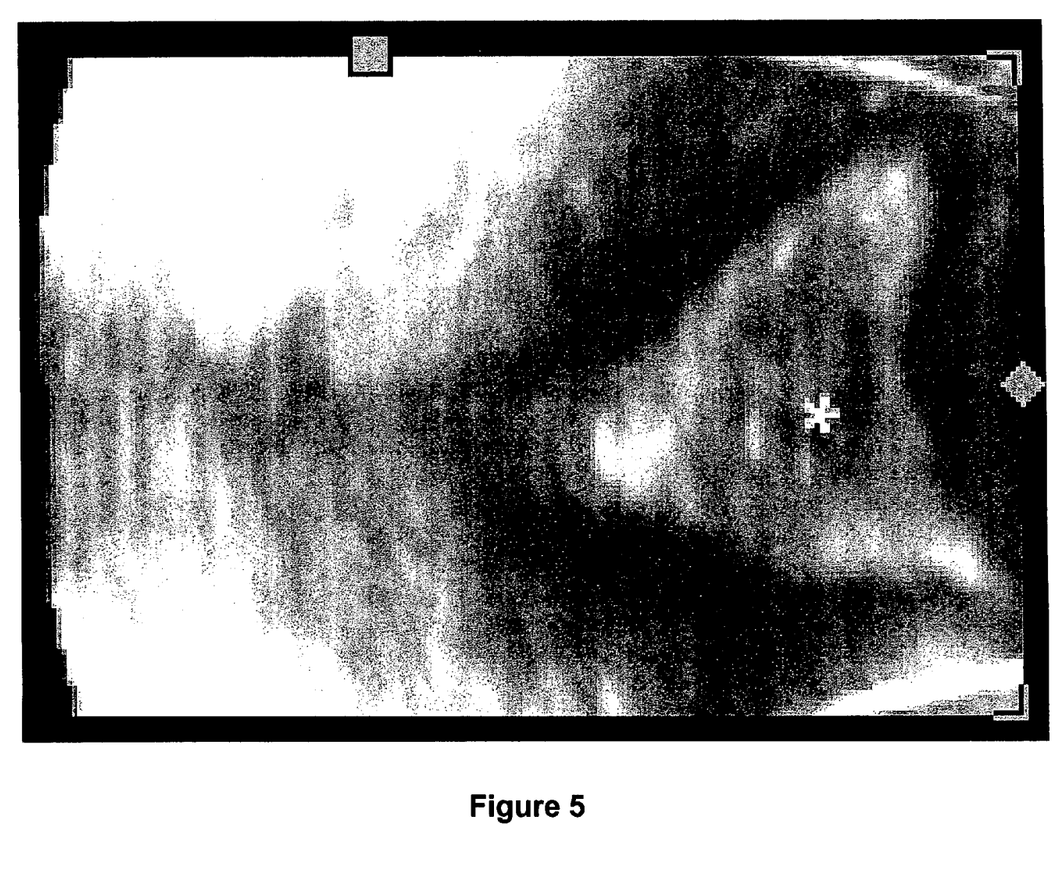
FIG. 5 shows a 3D ultrasound image of the uterine cavity. The Maximal implantation potential (MIP) point is marked with an asterisk.

Since the recent introduction of 3D ultrasound it is possible for the first time to visualize the uterine cavity as a whole (FIG. 5). 3D sonography can improve visualization of the uterus in patients with normal anatomy and especially in those with uterine anomalies, e.g. bicornuate uterus. Thus, the present invention provides a maximal implantation potential (MIP) point as a target for embryo transfers. The MIP point is defined below and is shown in FIGS. 1, 4 and 5.

The uterine cavity resembles an inverted triangle and the fallopian tubes open into the cavity, one in each of the upper regions of the triangle. The MIP is the intersection of these two imaginary lines, one originating in each fallopian tube, within the inverted triangle. In natural pregnancies, fertilization usually occurs in the ampullary segment of the fallopian tube and the pre-embryo then travels down to the uterus and usually implants in the anterior or posterior segment of the uterus close to it trajectory line, where the endometrium is the thickest and has the greatest blood flow. In patients undergoing In Vitro Fertilization, the fallopian tubes are bypassed, placing the embryos directly into the uterus. Therefore by using the MIP point, placement of the embryos occurs where nature intended.

Because of individual anatomical differences, the MIP point can be individually tailored. Further advances in 3D Ultrasonography as well as the introduction of the 4D Sonography make it possible to visualize the transfer catheter in real time as it moves towards its target: the MIP point.

Thus, the current invention involves the determination of the MIP point and the accurate release of embryos with the use of three and four dimensional sonography. As seen with the current invention, the use of three and four dimensional sonography allows the clinician to view the intrauterine cavity in a noninvasive manner. It is preferred that the clinician undertaking the techniques described herein receive training in the use of three and four dimensional sonography machines and current imaging modalities.

The technique of the current invention generally involves (a) expanding the bladder an appropriate amount to shift the uterus from an anteflexed position to lessen the angle between the cervix and the uterine cavity, (b) locating the "maximum implantation potential point" (MIP) with the aid of three dimensional sonography and (c) implanting the embryo in the uterus with the aid of four dimensional sonography. During this procedure, scanning is preferably transabdominal.

Before describing the procedure further, the MIP point is first discussed with reference to the cross-sectional view of the uterine cavity of FIG. 1. As shown, the uterine cavity generally resembles a triangle, and the fallopian tubes open into the uterine cavity in each one of the upper regions of the triangle. The fallopian tubes enter the uterine cavity at an angle of approximately 45 degrees on the left and 135 degrees on the right.

In natural pregnancies, the embryo travels down the fallopian tube into the uterine cavity. In connection with the current invention, it has been observed that in the majority of pregnancies, the embryo implants in the middle of the triangle in the anterior or posterior uterine wall. In that location, the endometrial lining is the thickest, which provides for increased blood flow and consequently increased potential for successful implantation. Accordingly, it is preferred to implant an embryo at that location.

The views provided by three and four dimensional sonography allow the clinician to determine where the MIP point is. More specifically, by extending lines depicting the axes of the fallopian tubes into the uterine cavity, it is seen that they intersect. Their intersection represents the MIP point where potential for successful implantation is optimal.

Figure 2:
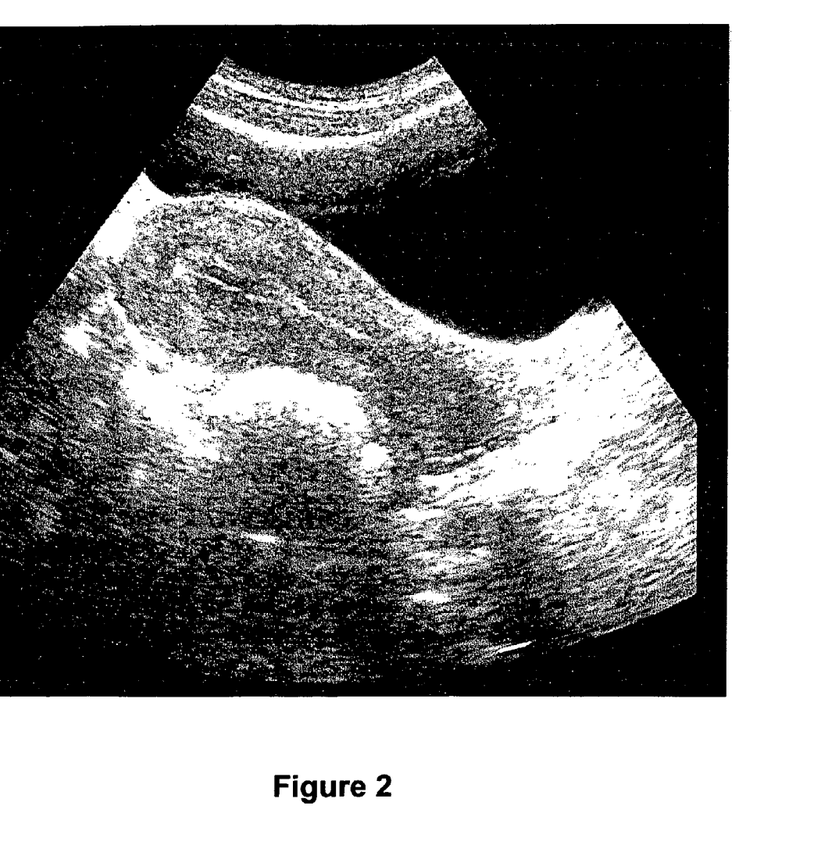
FIG. 2 is a conventional 2D ultrasound image of a uterus

It bears note that prior to the current invention, such views of the uterine cavity were not possible with two-dimensional ultrasound, shown in FIG. 2. Accordingly, the MIP point and the accuracy associated therewith were not even available for embryo transfer procedures.

Figure 3:
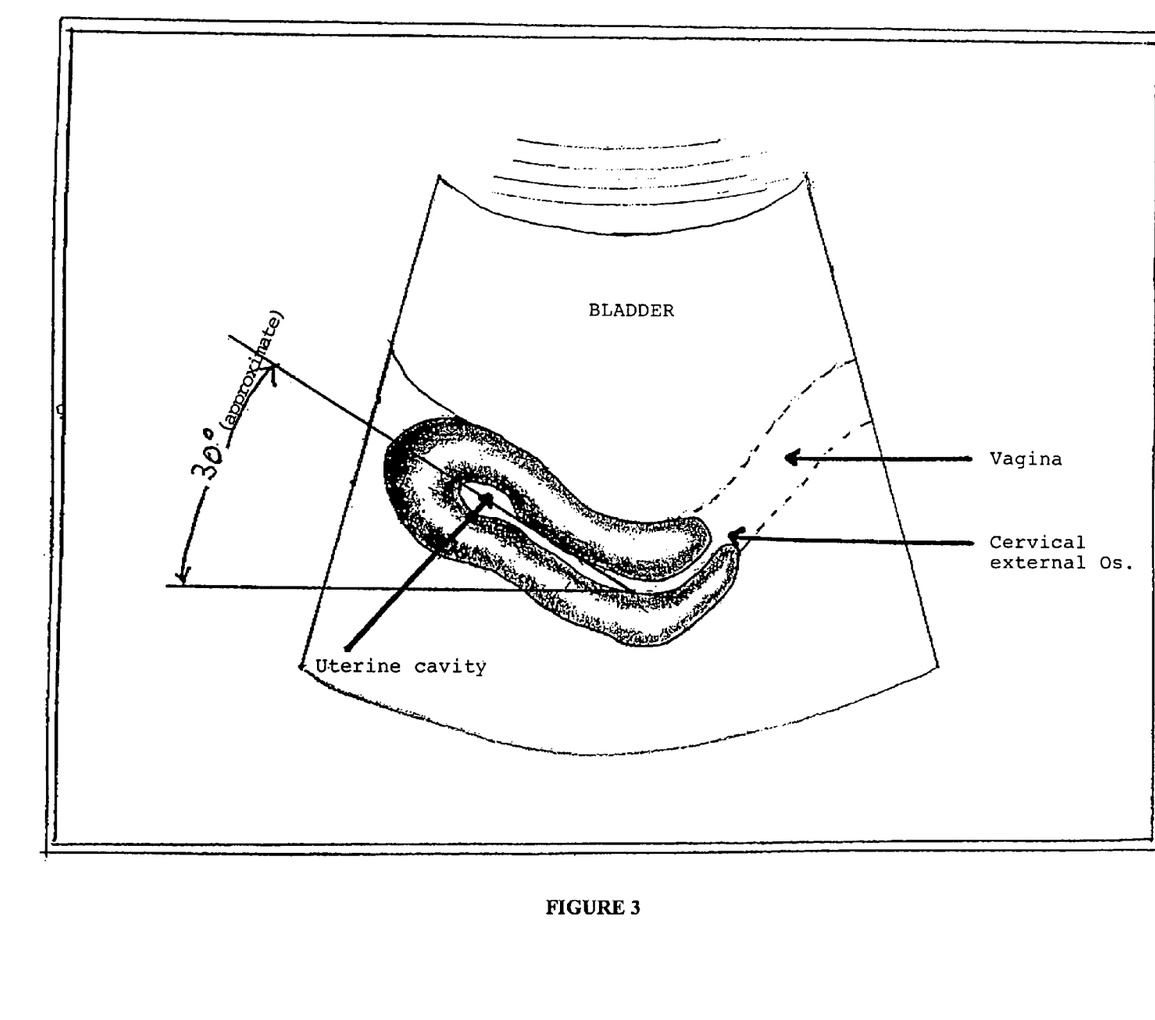
FIG. 3 is a cross-section of the uterine cavity.

The procedure of the current invention is now described in more detail. In the vast majority of cases, the uterus is naturally in an anteflexed position such that there is a sharp angle created between the cervix and the uterine cavity. Referring to FIG. 3, in an anteflexed position, the angle of the uterus would be 90 degrees or more as opposed to the 30 degree angle shown. This is problematic for the clinician since the catheter used to deliver embryos is typically soft and cannot be manipulated to engage curves.

Accordingly, it is preferred that the woman undergoing the embryo transfer drink an appropriate amount of water or other liquid to expand the bladder to move the uterus from an anteflexed position. For example, the patient may drink 32 oz. or other quantity of water or other liquid one hour (or some other suitable time) prior to the scheduled appointment. The angle may be viewed using two dimensional sonography. As shown in FIG. 3, it is preferred that the angle reach approximately 30 degrees for the procedure to occur.

Prior to embryo transfer, the sonography machine suited for use with the current invention should be adjusted to appropriate settings. Adjustments are generally necessary since each patient's physical attributes will differ. The adjustments may occur while the patient's bladder is filling to the appropriate level.

In a preferred embodiment, a sonography machine such as the GENERAL ELECTRIC VOLUSON 730 may be used. This unit provides both three-dimensional images and four dimensional, i.e., moving, images. The following protocol may be followed, but it should be noted that the following protocol is an example only, and is not intended to limit the current invention.

1) Turn on sonography unit.
2) Probe/Program Selection. Press the probe key. On the probe selection menu, probe RAB 2-5 3D may be used.
3) Application: Obstetrics.
4) Settings: 1. Trimester. Press the Freeze/Run key.
5) Scan 2D to ascertain adequate distension of the urinary bladder and desired position of the uterus.
6) Use the following settings on 2D before switching to 3D/4D.

Frequency resolution: Penet.
OTI: Adipose

7) Adjust Focal Point and depth. Focal point at the endometrial cavity. Enlarge image to include the full distance from the cervix to the uterine fundus.
8) Switching to 3D/4D, activate the Volume Mode (Hardkey).
9) Select 4D on the on the touch panel.
10) Display format: Select a ROI (left side of FIG. 4) with 4D image.
11) 3D/4D Setting: Touch Surface. 3D Orientation: 0 degrees.

12) Volume angle 25 degrees. Quality: High 2.

13) Position the Render Box to include the full length of the uterine cervix to endometrial cavity. Adjust size and content of the Render Box.

14) Start scanning. Reference image: In the ROI the uterine cavity will appear in a 15 degrees. Rotate the image slightly to become horizontal using the "Y" axis rotary key.

15) Using the Trackball raise the image in the ROI display to the level of the green line to overlap the Uterine canal and cavity.

16) On the 4D side the uterine canal and cavity will appear. Determine MIP. This may be accomplished by visualizing the intersection point of the lines representing the axes of the fallopian tubes.

17) Adjust thresholds, contrast and other color adjustments to obtain the best image.

It should be noted that the use of moving images provided by 4D is preferred. However, those portions of the protocols described herein involving 4D could be achieved using 3D.

The procedure associated with the actual embryo transfer is now more fully described. As a speculum is placed in the vagina by the performing physician, the uterine cavity will generally shift from the approximately 30 degree angle of FIG. 3 to zero degrees which is generally considered the optimal position for embryo transfer to occur. In any event, it is preferred that no curve or significant angle exists between the cervix and uterine cavity.

The following protocol may be followed for this aspect of the procedure. Again, it should be noted that the following protocol is an example only, and is not intended to limit the current invention. Several of the steps below reference FIG. 4 which represents a split screen on the sonography machine showing two dimensional and three/four dimensional views.

1) Start in two dimensional sonography and just adjust Focus and Size, and position of the Render box.

2) Once the catheter passes the Cervical Internal Os, switch to 3D/4D.

3) Raise the reference image to the top green line. Adjust if necessary using the Y axis key as shown in the left side of FIG. 4.

4) Simultaneously on the 4D side of the screen, the tip of the catheter will be seen as a bright light.

5) As the catheter moves forward toward the uterine cavity it can be followed on the 4D screen.

6) Advancing catheter is followed on the 4D screen. Slight adjustments may be continually made using the Track ball and its controls.

7) Once the catheter tip is over the MIP point, embryo(s) may be released as shown in FIG. 4 (right side).

8) At the time of the release an air bubble may be released. It will appear on the 4D display as a bright flash indicating the release of the embryo(s).

9) The retraction of the empty catheter may be followed using the 4D images. The air bubble will be seen left behind over the MIP point.

In another preferred embodiment, the present invention provides an integrated system for calculating and displaying the MIP point on the ultrasound machine display. In this embodiment of the invention, the operator is relieved of the task of locating the MIP point manually and the system automatically generates the MIP point for the physician. The system features a 3 or 4D ultrasound machine with a computer capable of calculating the intersection point of the lines extending from each fallopian tube and integrating the information with that obtained by ultrasonography of the thickness and/or perfusion of the endometrial lining of the uterine cavity. In a preferred embodiment of the system, the ultrasound machine is both a 3D and a 4D machine. In more preferred embodiments of the system, the GE Voluson 730 is adapted to perform the determination of the MIP point and to display it for the physician in real time, thus providing guidance for the implantation procedure.

Accordingly, the current invention provides systems capable of determining the optimal point of implantation for an embryo, thereby maximizing pregnancy rates resulting from IVF. The current invention also provides performing physicians with techniques and procedures to accurately release and implant embryos in the uterus at the location where the chances of pregnancy are optimal. The scope of the current invention extends to the use of other suitable sonography machines besides the units described above. Similarly, other protocols suitable for use with other machines are within the scope of the current invention.

REFERENCES

1. Kan A K, Abdalla HI, Gafar A H. Embryo transfer: ultrasound guided versus clinical touch. Hum Reprod 1999; 14:1259-61

2. Coroleu B, Carreras O, Veiga A. Embryo transfer under ultrasound guidance improves pregnancy rates after in-vitro fertilization. Hum Reprod 2000;15: 616-20

3. Wood E G, Batzer F, Go KJ, Gutman J, Corson SL. Ultrasound guided soft catheter embryo transfer will improve pregnancy rates in in-vitro fertilization. Hum Reprod 2000; 15: 616-20

4. Tang OS, NG EH, So WW. Ultrasound-guided embryo transfer: a prospective randomized controlled trial. Hum Reprod 2001; 11: 2310-5

5. Mansour RT, Aboulghar MA. Optimizing the embryo transfer technique. Human Reproduction 2002; 17:1149-1153.

6. Baba K, Isihara O, Hayashi N, Saitoh M, Taya J, Kinoshita K. Where does the embryo implant after embryo transfer in humans. Fertil Steril 2000; 73: 123-125

7. Frankfurter D, Trimachi J, Silva C, Keefe D. Middle to lower uterine segment embryo transfer improves implantation and pregnancy rates compared with fundal embryo transfer. Fertil & Steril 2004; 81: 1273-1277

8. Pope C, Cook E, Amy M, Novak A, Grow D. Influence of embryo transfer depthon in vitro fertilization and embryo transfer outcomes. Fertil & Steril 2004; 81: 51-58

9. Franco Jr JG, Martins AMVC, Baruffi RLR, Mauri AL, Petersen CG, Felipe V, Contart P, Pontes A, Oliveira JBA. Best site for embryo transfer: the upper or lower half of endometrial cavity? Hum Reprod 2004; 19: 1785-1790

10. Adams EC, Hertig AT, Rock J. A description of 34 human ova within the first 17 days of development. Am J Anat 1956; 98: 435-493.

EXAMPLES

The following examples are provided to better illustrate the claimed invention and are not to be interpreted as limiting the scope of the invention. To the extent that specific materials are mentioned, it is merely for purposes of illustration and is not intended to limit the invention. Although certain preferred embodiments of the current invention have been described herein, it will be apparent to those skilled in the art to which the invention pertains, that variations and modifications of the described embodiments may be made without departing from the spirit and scope of invention.

Example 1

A retrospective, observational study was conducted to evaluate the use of 3 dimensional/4 dimensional ultrasound in conjunction with the MIP point to facilitate embryo transfer and improve pregnancy rate.

Materials and Methods

Patients: 1222 patients underwent 3D/4D-Ultrasound guided embryo transfers at the IVF clinic. Embryo transfers were performed in all patients anywhere from two to six days after oocyte retrieval in the following manner.

Once the bladder was determined to be adequately full, by using abdominal 2D ultrasound initially, the 3D ultrasound mode was then employed revealing the uterine cavity, after which the MIP Point was identified. The physicians sterilized the perineum in the usual fashion using culture media and inserted a speculum into the vagina. Once the MIP was identified by the 3D/4D ultrasound machine, the physician inserted the transfer catheter that he or she deemed appropriate.

Figure 6:
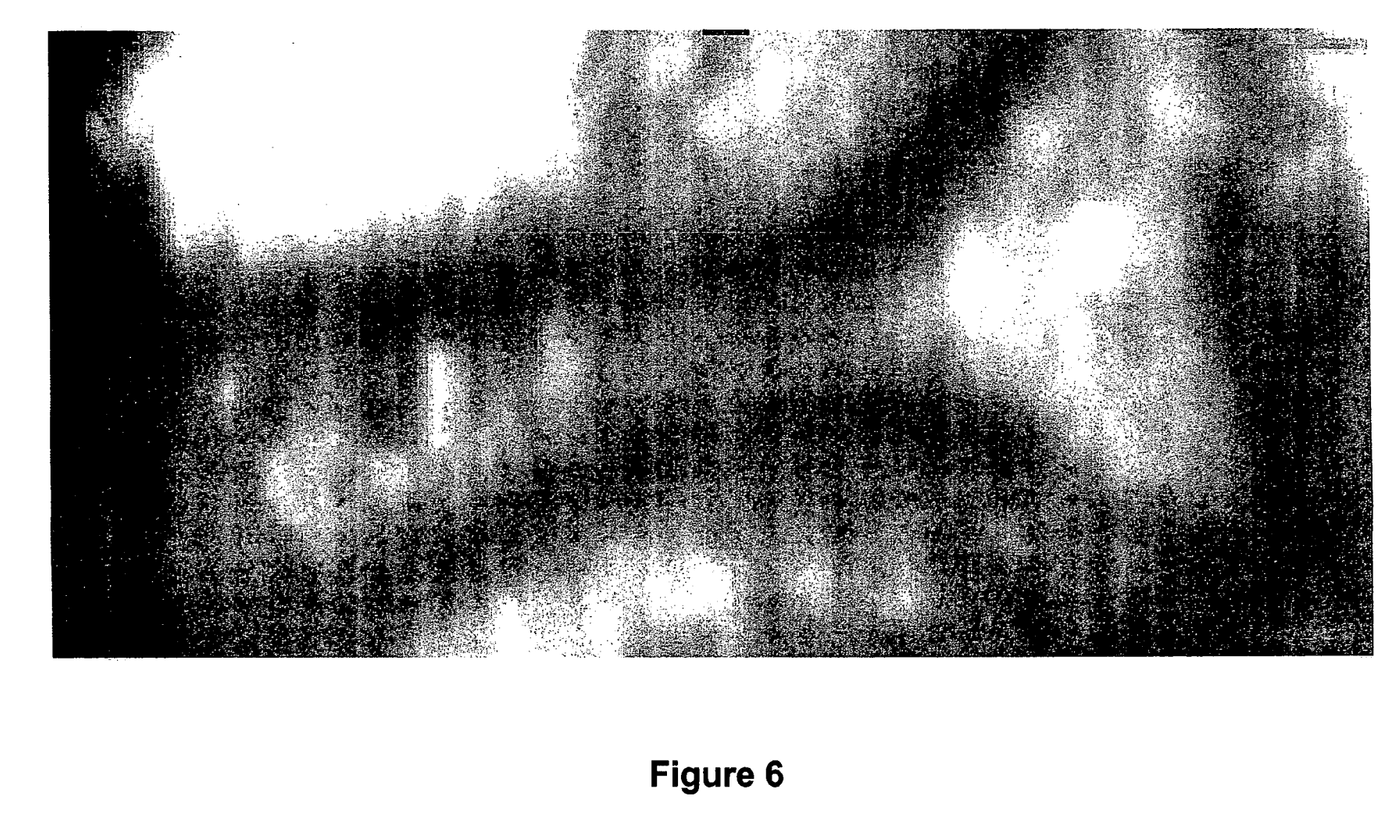
FIG. 6 shows how an embryo flash is confirmed on 3D ultrasound after transfer in area of maximal implantation potential.

The catheter tip was visualized during the entire insertion procedure and once the internal os was passed, the 4D mode was employed. This allowed us to follow the catheter tip in real-time on towards the predetermined MIP point. Once the tip of the catheter was over the MIP Point, the embryos were released inside the cavity and an embryo flash was visualized. (FIG. 6). The empty catheter was then gently withdrawn, and checked by the embryologist for remaining embryos. Once clearance was received, the speculum was removed and the patient was kept in a supine position for 30 minutes before discharged home.

Example 2

Results

During all embryo transfer procedures, the uterine cavity was well visualized using 3D/4D ultrasonography and the MIP point was well identified. During the time period evaluated, a total 1222 patients underwent 3D/4D ultrasound guidance utilizing the MIP point. Their average age was 37.6 years and the pregnancy rate was 36.66%. A total of 16 different physicians performed the transfers, with two of these physicians together performing 65% of the transfers. The ultrasound was performed by the same individual in all cases. Physicians reported improved visualization and were accepting to the incorporation of the 3D/4D sonography in the embryo transfer.

While the IVF technology and success rates have come a long way, there still remains room for improvement. The pregnancy rate is highly influenced by the quality of the embryos, the receptivity of the endometrium and by the transfer technique (5).

There is still no consensus of what the ideal choice for implantation is for embryos. In a study by Baba et al, embryos were transferred to the midfundal area in 60 patients. Among the 22 pregnancies, 80% of the embryos implanted in the areas to which they were transferred, while 20% implanted in other areas (6).

The location of embryo transfer in respect to the uterine anatomy also varies among physicians. Some studies have shown that the optimal location for embryo transfer is 0.5-1 cm away from the uterine fundus (3), while some believe that the tip of the catheter should be 1.5 cm from the uterine fundus (2). However, others have shown that transfer should be in the lower to middle uterine segment (7). In a different study by Pope et al, it was demonstrated that for every additional millimeter the embryos are placed away from the uterine fundus, the clinical pregnancy rate increases by 11% (8). In a recent randomized study by Franco et al, embryos were deposited in the lower or upper half of the endometrial cavity and there was no difference in pregnancy or implantation rates (9).

From early work on surgically removed uteri of Adams et al, implantation was found to take place in the upper half of the uterine cavity, most on the posterior wall of the uterus (10). This further supports the MIP Point as an advantageous spot, mimicking implantation in the general population. Since 3D/4D ultrasonography allows us to identify the MIP point with great ease, it is now possible to use the combination of MIP and 3D/4D sonography to accomplish embryo transfers accurately. Thus, the Maximal Implantation Potential Point can be readily identified and individualized for each patient. Embryo transfers at the MIP were associated with good implantation and pregnancy rates.

The invention claimed is:

1. A method of increasing pregnancy rates during embryo transfer using a sonography machine comprising:
    (a) turning on the sonography machine;
    (b) selecting a probe key from a probe selection menu;
    (c) scanning a monitor for a 2D image to ascertain adequate distension of the urinary bladder and desired position of the uterus;
    (d) adjusting settings for better visualization of the image;
    (e) adjusting focal point and depth such that the focal point is at the endometrial cavity;
    (f) changing the image from 2D to 3D/4D;
    (g) readjusting settings for optimal visualization of the image;
    (h) determining the MIP point by visualizing the intra uterine cavity and calculating the intersection point of lines representing the axes of the fallopian tubes.

2. A method of embryo transfer during in vitro fertilization comprising:
    (a) adjusting a 2D image on a sonography machine;
    (b) passing a catheter through the cervical os;
    (c) switching the image from 2D to 3D/4D;
    (d) adjusting settings for optimal visualization of the image;
    (e) determining the MIP point within the uterine cavity;
    (f) following the image of the catheter tip as it moves in the uterine cavity towards said MIP point; and
    (g) releasing the embryo from the catheter once the catheter tip is over said MIP point.

* * * * *

UNITED STATES PATENT AND TRADEMARK OFFICE
CERTIFICATE OF CORRECTION

PATENT NO. : 7,322,931 B2  Page 1 of 1
APPLICATION NO. : 11/131903
DATED : January 29, 2008
INVENTOR(S) : Robert Z. Gergely It is certified that error appears in the above-identified patent and that said Letters Patent is hereby corrected as shown below:

On the Title Page
The inventor's last name in item (12) is indicated as "Gergeley" and should be changed to --Gergely--.

On the Title Page
The inventor's name in item (76) is indicated as "Robert Z. Gergeley" and should be changed to --Robert Z. Gergely--.

Signed and Sealed this

Seventeenth Day of June, 2008

JON W. DUDAS
*Director of the United States Patent and Trademark Office*